United States Patent
Shibolet

(10) Patent No.: US 7,167,180 B1
(45) Date of Patent: Jan. 23, 2007

(54) AUTOMATIC PATH PLANNING SYSTEM AND METHOD

(75) Inventor: Omer Shibolet, Tel-Aviv (IL)

(73) Assignee: Algotec Systems Ltd., Ra'anana (IL)

( * ) Notice: Subject to any disclaimer, the term of this patent is extended or adjusted under 35 U.S.C. 154(b) by 0 days.

(21) Appl. No.: 09/622,731

(22) PCT Filed: Feb. 23, 1998

(86) PCT No.: PCT/IL98/00087

§ 371 (c)(1),
(2), (4) Date: Aug. 21, 2000

(87) PCT Pub. No.: WO99/42977

PCT Pub. Date: Aug. 26, 1999

(51) Int. Cl.
*G06T 15/00* (2006.01)

(52) U.S. Cl. .................. 345/474; 345/418; 345/419

(58) Field of Classification Search .............. 345/418, 345/419, 473, 474
See application file for complete search history.

(56) References Cited

U.S. PATENT DOCUMENTS 5,458,111 A  10/1995  Coin
5,611,025 A   3/1997  Lorensen et al.

FOREIGN PATENT DOCUMENTS

WO   WO 97/09690   3/1997
WO   WO 98/11524   3/1998

OTHER PUBLICATIONS

Paik, D.; "Automated Flight Path Planning for Virtual Endoscopy"; Medical Physics; vol. 25; No. 5; May 1998; pp. 629-637; XP002083445.
Rubin, G. et al.; "Perspective Volume Rendering of CT and MR Images: Applications for Endoscopic Imaging"; Radiology; Radiol. Soc. North America; vol. 199; No. 2; May 1996; pp. 321-330; XP 002083446.
Vining, D. et al.; "FreeFlight: A Virtual Endoscopy System"; First Joint Conference, Computer Vision, Virtual Reality and Robotics in Medicine and Medical Robotics and Computer-Assisted Surgery Proceedings; Mar. 19-22, 1997; pp. 415-416; XP002083447.
Aho, A. et al.; "Data Structures and Algorithms—The Single Source Shortest Paths Problem"; pp. 203-208; 1983.
Dougherty, E.; "An Introduction to Morphological Image Processing"; SPIE Press; pp. 42-48, 1992.
Young, T. et al.; "Handbook of Pattern Recognition and Image Processing"; Academic Press; pp. 224-225.

*Primary Examiner*—Phu K. Nguyen

(57) ABSTRACT

A method of path planning, comprising providing a dataset representing a cavity and a boundary; providing a plurality of points in said dataset, including at least a starting point and an ending point; and automatically determining a path between the starting point and the ending point, responsive to a penalty associated with passing through points in the cavity. Preferably, the penalty value associated with a point depends on a distance between the point and the boundary.

47 Claims, 4 Drawing Sheets

AUTOMATIC PATH PLANNING SYSTEM AND METHOD

RELATED APPLICATION

This application is a US national filing of PCT Application PCT/IL98/00087, filed Feb. 23, 1998.

FIELD OF THE INVENTION

The present invention relates to the display of three-dimensional medical imaging data sets, and in particular to automatic path selection for virtual endoscopy.

BACKGROUND OF THE INVENTION

In many medical situations it is necessary to obtain views of elongate cavities within the body, from within the cavities. Some common examples include blood vessels, intestines and the bronchi. An endoscope (and other, similar devices, collectively referred to herein as endoscopes) is a device which can be inserted into such a cavity and through which a small portion of the cavity can be viewed in real-time and with high-resolution.

Using physical endoscopes raises several problems. First, even though the endoscopic procedure is minimally invasive, it still involves inserting a surgical instrument into the body, which is both dangerous and painful. In addition, forcing a passage from the outside of the body and into the elongate cavity may cause tissue damage. Another problem is that the field of view and maneuverability of the endoscope are limited. Since the precise position of the endoscope and the point of view of the endoscope are difficult to determine, navigating in the body using an endoscope is difficult. This difficulty is paramount in inspection procedures, for example in colonscopy, where it is important to be sure that the entire colon was properly inspected.

A parallel procedure, known as virtual endoscopy, has been suggested, for example in U.S. Pat. Nos. 5,611,025 and 5,458,111, the disclosures of which are incorporated herein by reference. In virtual endoscopy the body is imaged using a three-dimensional medical imaging device, such as an ultrasound imager, nuclear medicine camera, magnetic resonance imager or a X-Ray computerized tomography scanner, to create a three-dimensional data set. Then, a graphics processor reconstructs views of internal cavities from the image data, as would have been viewed by a virtual endoscope traveling along a path in the cavity.

Manual planning of the path is a long process and while it might sometimes be desirable that the attending physician perform this task, he will seldom have the time to do so.

Two types of automatic path planning, where a user enters a starting point and an ending point and a computer generates a path connecting the two points, are known in the art. The above referenced U.S. Pat. No. 5,611,025 patent describes a method which determines a shortest path between two points in a tissue cavity, which path avoids obstacles, and which path may also be smoothed. However, such a path may pass very close to the obstacles. Another type of path planning method, shown for example in WWW Document "http://indigo2.rad.bgsm.edu/software/cp", the disclosure of which is incorporated herein by reference, attempts to plan a path along the middle of the passage, i.e., along a line known as the medial axis of the cavity. In one described embodiment, a plurality of medial axis paths are generated for a colon with a constriction (each path passing on a different side of the constriction) and a user selects the path which lets him see the most of the colon. One limitation of medial axis following is that the medial axis is not smooth, but is affected by the morphology of the passage, even if the passage is very wide. Thus, a bump in the passage wall causes a bump in the path.

SUMMARY OF THE INVENTION

It is an object of some embodiments of the present invention, to provide a method of automatic path planning for virtual endoscopy. Preferably, the planned path is used to generate a plurality of frames which can be viewed as a cine sequence.

Another object of some embodiments of the present invention is to provide a method of path planning which is based on a plurality of factors. Preferably, a penalty is assigned to each potential point along a path, for each factor, depending on the relative importance of the factor and/or on a deviation from the ideal value for the factor. Preferably, at least some of the factors are evaluated locally, for example, a distance of a point along the path from the boundary. Alternatively or additionally, at least some of the factors are evaluated-globally, for example, the length of the path. In a preferred embodiment of the invention, the penalty assigned for each factor is dependent on the morphology of the cavity, preferably the local morphology, such as the width. Alternatively or additionally, the penalty is dependent on characteristics of the path itself.

In accordance with a preferred embodiment of the invention, the factors may include one or more of: distance of path from the cavity boundary, sharpness of bends in the path, length of path, amount of twist of a generated field of view, viewing of certain desired points on the cavity boundary, speed of motion of viewed points, smoothness of path and amount of change between consecutive images. In a preferred embodiment of the invention, at least some of the factors are related to a comfort of viewing and/or quality of viewing. Alternatively or additionally, at least some of the factors are related to a diagnostic use of the generated view.

In accordance with a preferred embodiment of the invention, path planning includes one or more of: planning a trajectory of motion and/or velocity profile for a view origin point, planning a trajectory of motion and/or orientation for a line of sight from the view origin and planning viewing parameters for points along the trajectory. It should be appreciated that in some cases the view origin may be stationary, while the line of sight is in motion and vise-versa.

Another object of some preferred embodiments of the invention is to provide a method of planning a path for virtual endoscopy, in which the path is not limited to remaining in substantially the middle of a cavity through which the path passes. In a preferred embodiment of the invention, the path does not pass too close to the boundaries of—and/or obstacles in—the cavity.

Another object of some embodiments of the present invention is to provide a method of planning a path which is not adversely affected by small errors in the acquisition of the data, especially not affected by small holes in the boundary of the cavity.

Another object of some embodiments of the present invention is to provide a method of path planning for virtual endoscopy, in which the method is functionally dependent on morphological features of the cavity and/or of a path therethrough. In one preferred embodiment of the invention, the width of the passage is used for determining a desired amount of smoothing of a path. Alternatively or additionally, the width of the passage is used for determining a desired granularity of data and/or resolution of calculation for one or more steps of the method.

Another object of some embodiments of the present invention is to provide a method of path planning which directly uses voxel data, thereby avoiding the necessity to generate a surface representation and possibly add errors.

A method of path planning in accordance with a preferred embodiment of the invention, preferably includes at least some of the following steps:

(a) providing a three dimensional image data set, which includes a cavity;

(b) selecting a plurality of points, including at least a starting point and an ending point;

(c) determining a relatively direct and relatively short path between the starting point and the ending point, which path preferably takes into account the desirability of passing through different voxels of the cavity;

(d) optionally, smoothing the determined path;

(e) determining viewing parameters for each point along the path, preferably taking into account the distance of points along the path from the boundaries of the cavity and/or characteristics of the path;

(f) determining a rate of motion along the path, preferably for each point along the path, preferably taking into account the distance of points along the path from the boundaries of the cavity and/or characteristics of the path; and (g) optionally, optimizing the path.

In a typical embodiment of the invention, the image data set is a CT or MRI data set which is then segmented to yield information regarding cavities. In one preferred embodiment of the invention, a patient is injected with a blood contrast medium and then imaged using a CT device. The resulting three-dimensional data set is segmented using CT numbers, to differentiate between the contrast-enhanced blood and the other tissues. The area with the CT numbers corresponding to the blood is treated as a cavity. As can be appreciated, once an image is segmented, any portion of it can be defined as being "interior", i.e., a cavity and any other portion as being solid, i.e., "exterior". One example is nerve tissue vs. bone tissue in the spine. The boundary is a mathematical construct which defines the border between solid voxels and transparent voxels. As explained below, some preferred embodiments of the invention are especially forgiving with regard to the quality of the segmentation, especially if there are small holes in the boundary. Preferably, the area of interest is also limited to a region of interest select by a user. Alternatively or additionally, only voxels which are connected to the starting and ending points via "interior" voxels are considered to be in the cavity.

Typically, the above described method is implemented in a post-processing graphics station, which is preferably part of a medical imaging system. Alternatively, the station may be a separate viewing station.

In accordance with a preferred embodiment of the invention, the path determination is performed using a lower resolution and/or a different discretization grid than that of the voxel data and/or the resolution of the actual motion. For example, the path determination may be made in a grid having a unit size of more than one voxel, while the actual movement during the generated virtual endoscopy view may have a step size of half a voxel. Thus, in a preferred embodiment of the invention, there is a step of transforming from the grid used for path determination to the grid used for the actual motion. Preferably, this step is done before performing the smoothing. Alternatively, this step may be delayed, possibly even as late as the determination of the location of each viewing origin for each generated frame of the view. In a preferred embodiment of the invention, the smoothing is performed in a voxel type grid. Preferably, the determination of points at which views are generated, is performed by sampling and/or interpolating (preferably using a floating point notation) between whole voxel locations.

As used herein, the term "granularity" is used to refer to the size of voxels in a data set. The term "point" is used to refer to a location in the data set.

In a preferred embodiment of the invention, step (c) above is performed by applying an algorithm which finds a shortest distance path between the starting point and the ending points. However, instead of using a standard Euclidean distance function to determine a distance between two points in the cavity, the distance function preferably takes into account the desirability of the path going through a particular point in the cavity, by assigning different penalties to different points in the cavity. In one preferred embodiment of the invention, a penalty function depends only on the point itself, for example, the distance between the point and the nearest boundary, or another relationship between the point and the morphology of the cavity, such as the amount of local bend in the cavity. Preferably, only the local morphology is used for such a penalty function.

Additionally or alternatively, the penalty value associated with a point may depend on the path chosen or a portion of the path, for example, the amount of twist in the path. In a preferred embodiment of the invention, a relatively short duration is desired for the travel along the path. Thus, points which reduce the duration are preferred over points which increase the duration. In one example, the velocity of motion allowed through a certain point may be inversely dependent on the amount of bending in the path. Thus, points which increase the bend, increase the duration and have a lower desirability even though they shorten the path.

Alternatively or additionally, the penalty value associated with a point depends on the quality of a view possible from that point. The quality of view may depend on, inter alia, inclusion of points whose viewing is required, angular resolution of such points, available contrast, which is dependent on desired rendering parameters, angle between the point of view and the surface including the point of interest, angular size of such points of interest and type of movement of the view aiming point, while viewing.

In some preferred embodiments of the invention, the required quality of view is determined responsive to a required diagnostic activity at the points. Alternatively or additionally, the required quality of view is a user defined parameter, which preferably incorporates perceptual aspects of vision. In a preferred embodiment of the invention, the penalty value associated with a point depends on the rate of motion allowed through the point, which in turn may depend on the quality of the view desired. Alternatively or additionally, the point of view is determined based on the relative amount of time that certain portions of the cavity will be viewed as compared to other portions of the cavity. Locally modifying the velocity of the advance along the path changes the relative time that different parts of the cavity are viewed.

Thus, it can be appreciated that in accordance with some preferred embodiments of the invention, the path between the starting point and the ending point will not usually be the shortest possible path.

Although the above method has been described as including a multitude of steps, it should be appreciated that in some preferred embodiments of the invention, various of the steps may be combined and/or divided and/or their order changed. In a preferred embodiment of the invention, the content which the user desires to view; in particular, the content and quality of view which the user desires may determine the points along the path at which views are to be generated. In one preferred embodiment of the invention, the smoothing step is performed after the points of view are determined. Additional or alternatively, steps (e) and (f) are switched, so that the points of view are determined responsive to the desired velocity and the viewing parameters are determined only for these actual points of view. Alternatively or additionally, the selection of the actual points of view may be made dependent on the amount of local bend in the path and/or on other parameters, as described herein.

In preferred embodiments of the invention, only some of the steps of the method are applied. In one example, the path is provided by a user and the above described method is used only for determining the motion of the view aiming point. In another example, the above described method is used to check a user supplied path. In another example, the above described method may be used to add a point in the middle of an existing path and/or to change the trajectory of a view aiming point of an existing path.

In accordance with another preferred embodiment of the invention, the above described method is used in a semi-automatic manner. Preferably, the method suggests a path which meets, preferably at least semi-optimally, various restrictions proposed by a user. In one example, a user can specify a cavity, a plurality of goal points, a plurality of points to be viewed, a minimum allowed distance between a path and a boundary of the cavity. The method will generate a suggested path, preferably indicating points along the path and/or viewed areas which do not meet the requirements. Alternatively or additionally, the user might specify points of interest which should be viewed under good viewing conditions. In this and other embodiments, the method preferably indicates points which will not be viewed. Alternatively or additionally, the method preferably indicates points which are viewed for too short a time and/or which move along the viewing area on the screen at a velocity above a maximum allowed velocity (angular velocity)

In preferred embodiments of the invention, at least one of two types of restrictions may be supplied, rigid and flexible. Rigid restrictions may not be violated. Flexible restrictions may be violated, for a penalty, however, it is generally preferred that they not be violated (if possible). For example, a flexible restriction on the path, to be at least 3 voxels away from a boundary, will take part in a tradeoff with the allowed amount of bending in the path. A rigid restriction will not allow such a tradeoff and will cause a larger amount of bending in the path. As can be appreciated, overly rigid restrictions may cause some of the above described methods to fail in finding a path. Preferably, rather than fail, the system requests a user to soften or delete certain limitations. Alternatively, the system automatically proposes a minimally violating path which violates a minimum of rigid restrictions. Preferably, the rigid restrictions are ranked. Preferably, the system indicates to the user if any rigid restrictions were violated in a particular path. Preferably, the violating path is shown to the user so that he can assess the effects of the violation.

In accordance with a preferred embodiment of the invention, the penalty function is dependent on the distance of voxels from the boundary of the cavity. In one preferred embodiment of the invention, the penalty function is strongly prejudiced against voxels which are close to the boundary, but voxels which are over a certain minimum distance from the boundary may have a substantially same penalty. One example of such a function is one exponentially inversely related to the actual distance. In another example, there is a distance cutoff, above which the function is a constant. Alternatively, the penalty function may be calculated using a look-up table.

In one preferred embodiment of the invention, the distance from the boundary of the cavity is calculated by a wave propagation method from the boundaries. In accordance with another preferred embodiment of the invention, the distance is calculated by sequentially eroding the cavity with balls of increasing radius, whereupon at each radius step, all the un-eroded voxels are marked as having a distance of at least the eroding radius. In a preferred embodiment of the invention, erosion with large balls is approximated by erosion with a plurality of small balls, whose sum of radii equals the radius of the large ball. In a preferred embodiment of the invention, at least some steps of the erosion process are performed by eroding the result of a previous step with a small ball (having a radius smaller than r, the current step).

In accordance with a preferred embodiment of the invention, not all the voxels in the data set are taken into account, as possible points along the path, when planning the path. Preferably a subset of the points is selected, such that the computational complexity of path-finding may be substantially reduced. In a preferred embodiment of the invention, voxels which would probably not form part of the path, for example as a result of having a high penalty, are removed from consideration. In a preferred embodiment of the invention, such a subset of voxels is generated by skeletonization. Skeletonization is a process which attempts to reduce the number of voxels in an object, while maintaining the morphological features of the object. The product of the skeletonization process is a set of voxels which are at centers of maximal balls which can fit into the cavity. This set in not necessarily connected. Further, since many voxels are dropped, it is possible that a voxel will not have any neighbors. In a preferred embodiment of the invention, neighbors of a voxel, for purposes of path determination, are considered to be those voxels within a short distance. Preferably, a determination is made whether there is a short path between the two points which only passes through interior voxels. This distance is preferably dependent on the distance of the voxel from the boundary and/or on the typical width of the cavity. Alternatively, the distance to many points may be determined, for each voxel in the skeleton.

In a accordance with a preferred embodiment of the invention, skeletonization is performed based on the results from each stage of erosion. In one preferred embodiment of the invention, an skeletonization of radius r is achieved by first eroding with a ball with radius r, then opening (eroding+dilating) with a ball of radius 1, i.e., by dilating the result of the r+1 eroding step, described above.

In accordance with a preferred embodiment of the invention, the data set granularity is reduced, to increase the speed of the algorithm. In accordance with one preferred embodiment of the invention, the granularity is reduced by a fixed ratio. Alternatively or additionally, the granularity is reduced by different ratios, for different parts of the image data, preferably, depending on the morphology of the cavity. Alternatively or additionally, the granularity is chosen responsive to a narrowest passage through which the path passes. Accordingly, in a preferred embodiment of the invention, a preliminary non-optimal path is determined, to assess path passage characteristics which may affect the desired granularity. A final granularity is then preferably determined, using the determined characteristics, for use with an optimal path finding method.

In a preferred embodiment of the invention, the granularity does not affect all the steps of the algorithm. In one preferred embodiment of the invention, the granulation is embodied by determining the step size and/or the minimal radius used in the erosion and/or skeletonization step. Alternatively or additionally, the local granularity is made inversely related to the penalty function, in the path finding step. Preferably, in voxels where there are large changes in the penalty function and/or where the penalty function is high, the granularity is finer. Preferably, the granularity is anisotropic.

In a preferred embodiment of the invention, the amount and/or type of smoothing is dependent on the local width of passages. Path portions which pass through narrow passages are preferably not smoothed at all, to reduce the chance of the path entering a cavity boundary and/or passing to close to a boundary.

In a preferred embodiment of the invention, the line of sight for viewing is determined using the viewing origin and an aiming point, around which a viewport is preferably centered. Preferably, the aiming point is along the path. Preferably, the distance between the viewing origin and the aiming point is dependent on the amount of local bending and/or on the distance to the nearest boundary in the path. Preferably, the distance between the viewing origin and the aiming point is determined in such a manner as to maintain the twisting of the viewport below a certain level.

In a preferred embodiment of the invention, a user can control some or all of the viewing parameters while the view is being generated. Such control preferably includes one or more of: stopping the motion of the viewing origin, changing its velocity and/or the overall velocity of the viewing origin, marking points of interest, changing the aiming point and/or its trajectory of motion and changing the viewport. Preferably, the user can continue the generation of the view from the point at which he started deviating from the original planned path.

It should be appreciated that various aspects of the present invention are not related to voxel-type data representation and/or to any particular shape and/or consistency of size of the voxels. In a preferred embodiment of the invention, the image data is manipulated, at least in part, as polygons which describe surfaces, rather than as voxels. In such a case the path is preferably determined utilizing a resolution grid, rather than based on a voxel size, as in some other preferred embodiments of the invention.

There is therefor provided in accordance with a preferred embodiment of the invention, a method of path planning, comprising:

providing a medical imaging dataset representing a cavity and a boundary;

providing a plurality of points in said dataset, including at least a starting point and an ending point; and automatically determining a path between the starting point and the ending point, responsive to a penalty associated with passing through various points in the cavity.

Preferably, said penalty function is responsive to a morphology of the cavity. Preferably, said morphology comprises a width. Alternatively or additionally, said morphology is a local morphology.

In a preferred embodiment of the invention, said penalty function is responsive to the path. Preferably, said penalty function is responsive to an amount of local bending of the path.

In a preferred embodiment of the invention, automatically determining a path comprises automatically determining a trajectory of an origin of a viewport.

In a preferred embodiment of the invention, providing a plurality of points comprises providing a trajectory. Alternatively or additionally, automatically determining a path comprises automatically determining a trajectory of an aiming point. Alternatively or additionally, automatically determining a path comprises automatically determining an angular orientation of a line of sight, relative to a path traveled by a viewport origin. Alternatively or additionally, automatically determining a path comprises automatically determining an angular orientation of a line of sight, relative to a path traveled by a viewport origin, responsive to a local width of the cavity. Alternatively or additionally, automatically determining a path comprises automatically determining an angular orientation of a line of sight, relative to a path traveled by a viewport origin, responsive to a local bend of the path.

Alternatively or additionally, automatically determining a path comprises automatically determining at least one viewing parameter along a trajectory of a view origin point. Alternatively or additionally, said penalty depends on a viewing quality possible from a point. Preferably, said viewing quality depends on human perceptual abilities. Alternatively or additionally, said viewing quality depends on a specific task to be performed with said path.

In a preferred embodiment of the invention, the method includes smoothing the path. Preferably, said smoothing is dependent on a local width of the cavity, at the smoothed portion of the path.

In a preferred embodiment of the invention, the method includes automatically repeating at least said automatically determining a path between said starting and ending points.

In a preferred embodiment of the invention, the invention includes providing at least one user-provided limitation on said path determination. Preferably, automatically repeating comprises automatically repeating automatically determining a path, responsive to at least one user-provided limitation. Alternatively or additionally, said at least one limitation comprises a rigid limitation. Alternatively or additionally, said at least one limitation comprises a flexible limitation. Alternatively or additionally, the method comprises indicating to a user which limitations are not met.

In a preferred embodiment of the invention, the method comprises selecting a data granularity level for said path determination. Alternatively or additionally, automatically determining a path comprises evaluating a penalty function for the points. Preferably, said penalty function is dependent on the distance of the point from a boundary of the cavity. Preferably, said penalty function is lower for points which are further from the boundary. Alternatively or additionally, said penalty function has a substantial rate of increase when approaching said boundary. Alternatively or additionally, said penalty function has a low rate of change away from said boundary. Alternatively or additionally, the method comprises determining said distance by erosion of the dataset. Alternatively, the method comprises determining said distance by wave propagation from the boundaries of said cavity.

In a preferred embodiment of the invention, said determining a path comprises determining a relatively short path. Preferably, a relatively short path comprises a shortest path which takes into consideration the penalty value associated with the various locations. Alternatively or additionally, automatically determining a path comprises generating a graph representing at least a portion of the cavity. Preferably, said path is determined by applying a path finding method to the graph and wherein said portions of said graph are generated only when needed by said method. Alternatively or additionally, automatically determining a path comprises determining a path using Dijkstra's shortest path finding method on said graph. Alternatively or additionally, said graph includes only a subset of voxels in said cavity. Preferably, said graph comprises substantially only a skeleton of said cavity. Preferably, said skeleton is found utilizing data from erosion of the cavity, which erosion is utilized to determine a distance of interior points from said boundary.

In a preferred embodiment of the invention, said dataset is represented by voxels. Alternatively or additionally, said boundary is represented by polygons. Alternatively or additionally, said dataset comprises a CT dataset. Alternatively or additionally, said dataset comprises an MRI dataset. Alternatively or additionally, said dataset comprises a NM dataset.

In a preferred embodiment of the invention, said boundary has small holes therein and wherein said path does not pass through holes narrower than a predetermined width. Preferably, said predetermined width is dependent on a morphology of the cavity.

There is also provided in accordance with a preferred embodiment of the invention, a method of path planning, comprising:

providing a medical dataset representing a cavity having a plurality of bends and a boundary;

providing a plurality of points in said dataset, including at least a starting point and an ending point;

automatically determining a path between the starting point and the ending point, wherein said path does not remain substantially in a medial axis of the cavity and does not approach closer than a predetermined distance to said boundary, in at least two of said bends.

Preferably, said dataset is represented using voxels and wherein said path does not approach closer than one voxel to said boundary. Alternatively, said dataset is represented using voxels and wherein said path does not approach closer than three voxels to said boundary. Alternatively, said dataset is represented using voxels and wherein said path does not approach closer than one tenth the local width of said cavity, to said boundary. Alternatively, or additionally, said dataset is represented using voxels and wherein said path does pass through holes in said boundary which are narrower than a predetermined width.

There is also provided in accordance with a preferred embodiment of the invention, a method of skeletonizing a dataset including a cavity and a boundary thereof, comprising:

eroding said cavity, using balls of increasing radius R;

determining a distance of points interior to the cavity, from the boundary, utilizing said erosion;

opening said eroded cavity, for each radius R, using a ball of radius 1; and accumulating the points which are removed from said eroded cavity by said opening, to form a skeleton.

Preferably, erosion by a ball R comprises eroding the result of eroding with a ball of radius R−1, with a ball of radius 1.

There is also provided in accordance with a preferred embodiment of the invention, a method of path planning, comprising:

providing a dataset representing a cavity and a boundary;

providing a plurality of points in said dataset, including at least a starting point and an ending point; and automatically determining a path between the starting point and the ending point, responsive to a penalty associated with passing through various points in the cavity.

Preferably, said penalty function is responsive to a width of the cavity. Alternatively or additionally, said penalty function is responsive to an amount of local bending of the path. Alternatively or additionally, automatically determining a path comprises evaluating a penalty function for the points. Preferably, said penalty function is dependent on the distance of the point from a boundary of the cavity. Preferably, said penalty function is lower for points which are further from the boundary.

In a preferred embodiment of the invention, said determining a path comprises determining a relatively short path. Preferably, a relatively short path comprises a shortest path which takes into consideration the penalty value associated with the various points. Alternatively or additionally, automatically determining a path comprises generating a graph representing at least a portion of the cavity and wherein said path is determined by applying a path finding method to the graph and wherein said portions of said graph are generated only when needed by said method.

BRIEF DESCRIPTION OF THE DRAWINGS

The present invention will be more clearly understood from the following detailed description of the preferred embodiments of the invention and from the attached drawings, in which.

DETAILED DESCRIPTION OF THE PREFERRED EMBODIMENTS

Figure 1A:
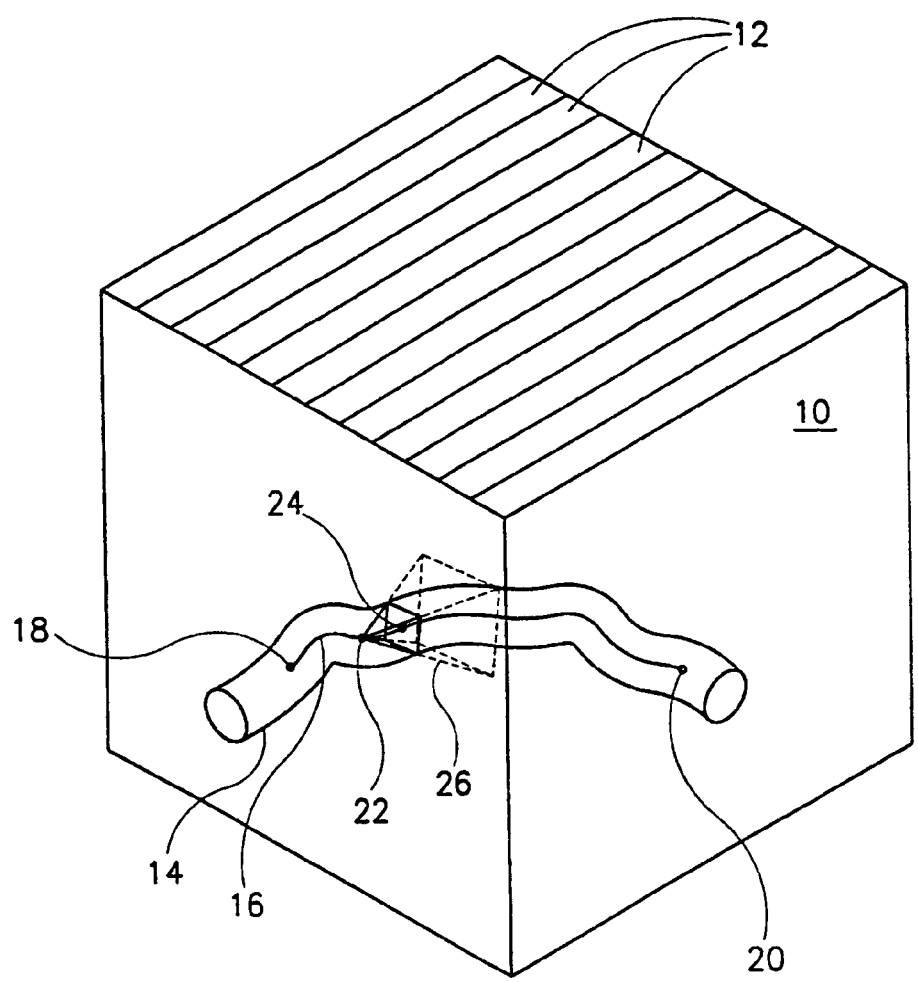
FIG. 1A is a schematic illustration of a three-dimensional data set, including a cavity and a path through the cavity.
Figure 1B:
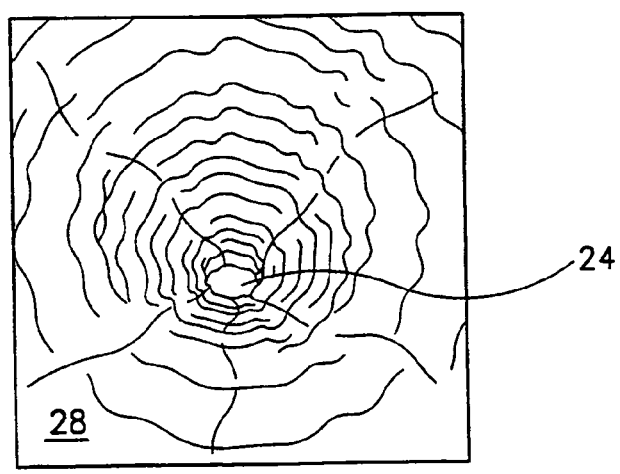
FIG. 1B is a schematic illustration of a view seen through a viewport on a particular point along the path of FIG. 1A.

FIG. 1A is a schematic illustration of a three-dimensional data set 10, including a cavity 14 and a path 16 through the cavity. Data set 10 usually comprises a plurality of image slices 12, however, in many cases, it is desirable to view portions of the data set, as seen from a view origin point 22 along path 16. This view is defined by a view origin point 22 staring at a view aiming point 24 through a viewport 26. In some cases, it may be more convenient to describe the viewport as being centered around a line of sight between the view origin point and the aiming point. It should be appreciated that the view may be clipped, so that voxels that are very close to the view origin point are not viewed. In an orthogonal projection, the view origin point can be in one of many places along the line of sight, however a fixed location is usually supplied. FIG. 1B is a schematic illustration of a view 28 seen through viewport 26.

A system, in accordance with some preferred embodiments of the invention, provides automatic and/or semi-automatic methods of planning a path, such as path 16, so as to best view portions of data set 10.

The actual view when traveling along path 16 is affected of a plurality of variables, including:

(a) the trajectory, angular orientation and velocity profile of view origin 22;

(b) the trajectory, angular orientation and velocity profile of view aiming point 24;

(c) viewport parameters, such as size, aspect ratio and distortion type and amount; and (d) additional information displayed in conjunction with data from data set 10.

In accordance with a preferred embodiment of the invention, it is desirable that the generated view be such that it aids diagnosis, maintains spatial orientation, takes into account human perceptual abilities and/or human viewing comfort. Preferably, the generated view is made more optimal by taking into account the particular characteristics of cavity 14, path 16, data set 10, a required use for the generated view and/or desired "illumination" characteristics, including intensity, location, movement, fog and decay with distance. In a preferred embodiment of the invention, the generated view is used as an aid for surgery, for example, for rehearsing for a surgical procedure or even during surgery, to aid in orientation and tissue identification.

In a preferred embodiment of the invention, the quality of the generated view is required to meet certain criteria and/or a composite criterion, at each point thereof. Alternatively or additionally, an average criterion is set, such that the entire path as a whole must meet certain standards. One example of an average criteria arises when determining the velocity of motion along path 16. An existing velocity profile may be multiplied by a factor so that the average viewing quality is at a predetermined level. Alternatively, the factor may be chosen so that the worst point along the path, or that no more than a predetermined percentage of the path, has a lower than desired viewing quality.

Figure 2:
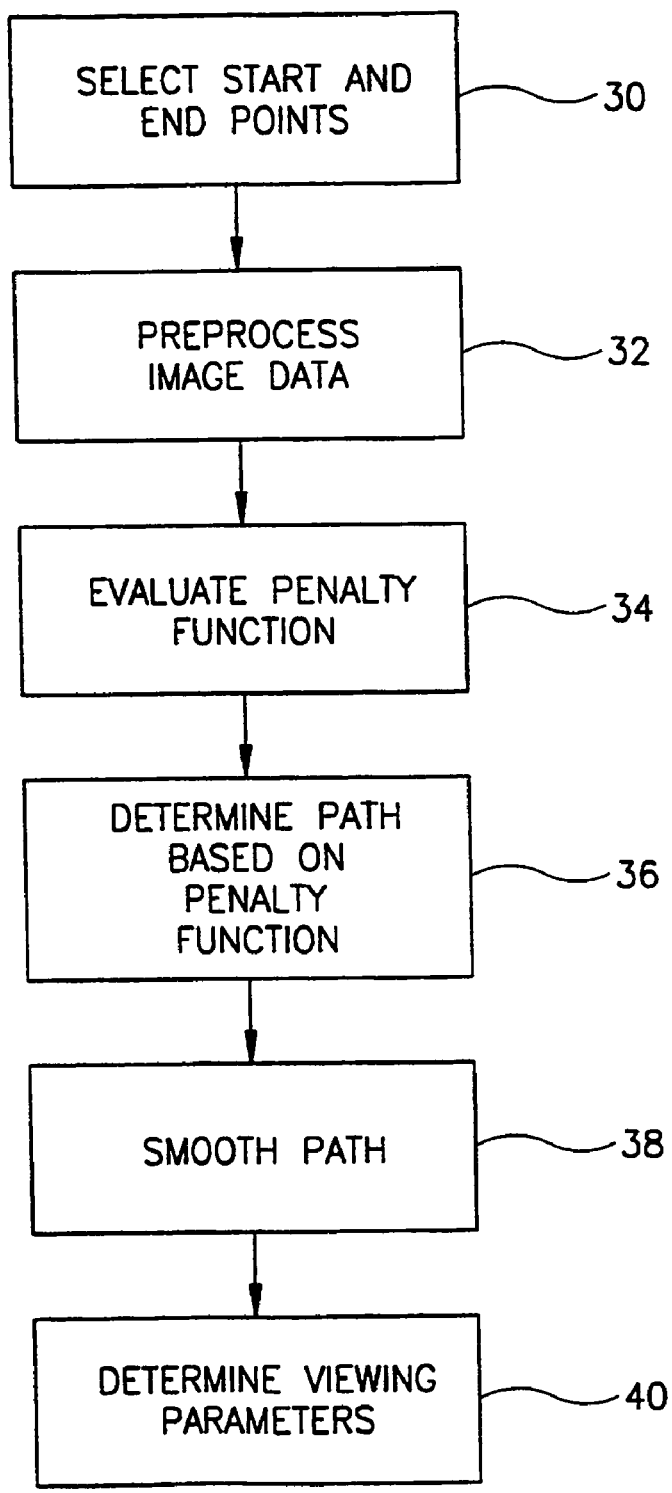
FIG. 2 is a flowchart of a method of path planning, in accordance with a preferred embodiment of the invention.

FIG. 2 is a flowchart of a method of path planning, in accordance with a preferred embodiment of the invention. A plurality of goal points are chosen (30), which preferably includes at least a starting point 18 and an ending point 20 (FIG. 1A). Alternatively or additionally to goal points, other restrictions, such as described below, may be entered. Responsive to the required path planning task, the data is then preferably preprocessed (32), for example by selecting a granularity or by segmenting the data into cavity and non-cavity tissues. In some preferred embodiments of the invention, at least part of the preprocessing, for example the segmentation, is performed prior to the selection of restrictions.

Although, in the subject, the boundary of a cavity is usually differentiated, many medical imaging techniques do not have a sufficient resolution to separate the thin boundary tissues. Rather, the boundary is typically treated as a mathematical surface one side of which includes only voxels of the interior of cavity and on the other side of which includes only voxels of the exterior of the cavity. Thus, any transition between interior voxels and exterior voxels must penetrate a boundary.

In a preferred embodiment of the invention, a penalty function is evaluated for at least some of the voxels in the cavity (34) before or during the determination of the path. Thus, it needs to be evaluated only once for a plurality of path planning sessions in the same cavity. However, in some preferred embodiments of the invention, the penalty function may be evaluated while determining the path. Alternatively, a penalty function may be evaluated prior to selecting at least some of the restrictions on the path. In a preferred embodiment of the invention, the penalty function is based on a typical width of the cavity. In one preferred embodiment of the invention the typical width is defined globally. Preferably the typical width is the average between half the maximum radius used for erosion and the number of erosion steps required to remain with only half the voxels un-eroded. Alternatively, the typical width is defined locally, for example by averaging only over the voxels included in a maximum ball which includes the current voxel (for which the local typical width is being determined). In a preferred embodiment of the invention, where the typical width is 5, the penalty function has the following dependency on the distance from the boundary:

| distance | 1      | 2     | 3   | 4   | 5   | 6   | 7   | n > 7           |
|----------|--------|-------|-----|-----|-----|-----|-----|-----------------|
| penalty  | 30,000 | 4,000 | 800 | 500 | 300 | 200 | 170 | 170* $0.95^{(n-7)}$ |

In a preferred embodiment of the invention, the penalty function is evaluated only when required and not calculated in advance for the entire data set. In one preferred embodiment of the invention, arcs are connected and vortexes added to the graph only if necessary, and only then does a penalty function need to be evaluated. Further, the distance may also be calculated using lazy evaluation techniques, especially, if the data is stored using a polygonal representation.

Using the penalty function, a path is determined (36). A certain voxel is included in the path depending on the relative penalty of that voxel as compared to other available, neighboring voxels. Preferably, the path is determined using Dijkstra's method for finding a short path. In this embodiment, the penalty is preferably taken into account as a weight on an arc connecting the current voxel with the growing end of the path. This method is described in "Data Structures and Algorithms", by A. V. Aho, J. E. Hopcroft and J. D. Ulman, pp. 203–208, published by Addison-Wesley in 1983, the disclosure of which is incorporated herein by reference. In some preferred embodiments of the invention, for example where a penalty is assigned for sharp bends in the path, the penalty function is a function of the path, so that it must be evaluated in conjunction with the path determination. In some preferred embodiments of the invention, other types of path determination methods are used. It should be appreciated that in some cases a shortest path, even with respect to the penalty function, will not be found, rather a significantly short path will be found.

Figure 3:
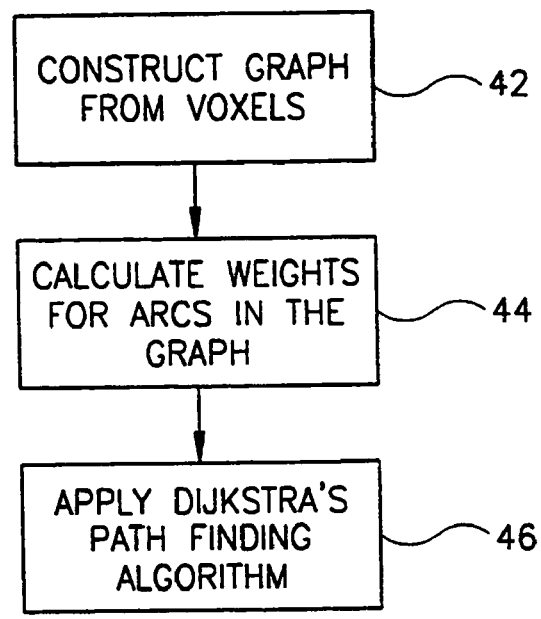
FIG. 3 is a flowchart of a method of finding a short path between two voxels, in accordance with a preferred embodiment of the invention.

FIG. 3 is a flowchart of a method of finding a short path between two voxels, preferably with a low overall penalty, in accordance with a preferred embodiment of the invention. The voxels through which the path can pass are organized into a graph, where each voxel is a vortex and arcs are defined connecting neighboring voxels. In a preferred embodiment of the invention, the weight of the arcs are determined by the penalty function. Additionally or alternatively, the weight may take into account the real distance between voxels centers, however, in some preferred embodiments of the invention, the distance between neighboring voxels is defined to be a unit length. In skeletonization embodiments of the invention, the arc weight preferably takes into account, the penalty associated with all the voxels between the two voxels from the skeleton. Alternatively, the penalty at one or both of the voxels is multiplied by the distance between the voxels. In some preferred embodiments of the invention, the penalty function describes the desirability of the path going between two neighboring voxels, rather than the desirability of the path passing through a particular voxel. In some preferred embodiments of the invention, some voxels have no penalty assigned thereto.

Referring back to FIG. 2, after the path is determined, it is preferably smoothed (38). In accordance with a preferred embodiment of the invention, the amount of smoothing is dependent on the width of the passage thorough which the path passes. For example, the path is not smoothed in very narrow passages, so as to lessen the danger of the smoothed path passing though a boundary.

Thereafter, viewing parameters, such as the motion of the viewport and viewport parameters are preferably determined (40), so as to completely define the path.

The above described method can be implemented in many ways. Usually, there is a tradeoff between accuracy and computation time. In some cases, there is also a tradeoff with the complexity of the implementation. One example of a tradeoff between accuracy and computation time is the granularity of the data set used for the path determination. Reducing the granularity of the data set, reduces the number of voxels and thus shortens the computation time required to apply the method. The granularity of the data may be reduced by increasing the voxel size by a fixed ratio and rebinning the data set into the new voxels. Alternatively, each portion of the data can be provided with a different granularity. In a preferred embodiment of the invention, a user is provided with several choices of granularity.

It should be appreciated that there are several steps of the method for which the data and or computation granularity may be changed, and there is no necessity that the same granularity be used for all the steps. For example, in a preferred embodiment of the invention, described below, the distance function is evaluated by erosion of the cavity. Granularity can be set by selecting a minimum ball size and/or a radius increment, thereby reducing computational time, but decreasing the quality (accuracy) of the determined distance. Additionally or alternatively, the parameters of ball radius size and increment can be set for a skeletonization step, described below. Additionally or alternatively, in a preferred embodiment of the invention, not all the voxels are used as vortexes in the graph used for Dijkstra's method, for example, by averaging neighboring voxels, or by skeletonization, described below. In each of the above described granularity decisions, the granularity can be made dependent on local characteristics, such as local passage width.

Figure 4:
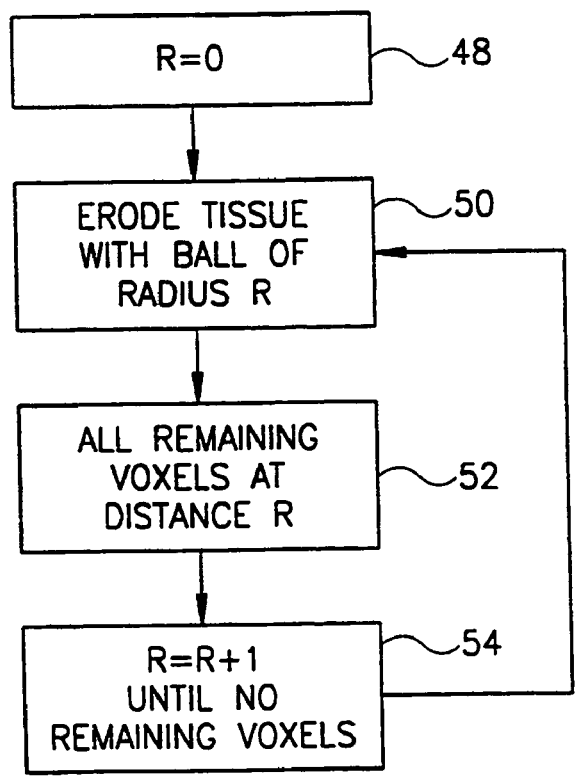
FIG. 4 is a flowchart of a method of calculating a distance function between each point in a cavity and the boundaries of the cavity, in accordance with a preferred embodiment of the invention.

FIG. 4 is a flowchart of a method of calculating a distance function between each point in a cavity and the boundaries of the cavity, in accordance with a preferred embodiment of the invention. In a preferred embodiment of the invention, the distance function is calculated by erosion of a copy of the dataset with balls of increasing radius. First, all the voxels in the cavity are assigned a distance of zero. This may also be done by erosion with a ball of radius zero. An erosion radius r is set to a minimum erosion radius (48), preferably zero, but possibly other small values, such as one or two. Next, the cavity is eroded with balls of the erosion radius (50). All the un-eroded voxels in the cavity are assigned a distance of r (52). The process is repeated with an incremented radius r (54), if there are any remaining interior voxels. Preferably the increment in the radius is one, however, other increments may be used, preferably as a way of modifying the granularity.

In accordance with a preferred embodiment of the invention, erosion with a ball of radius r is approximated by erosion with a plurality of balls whose sum of radii is r. Preferably, at least some of the steps in the erosion process are performed by eroding the result of a previous step with a small radius ball, rather than by eroding the original cavity with a single ball of radius r. Preferably the small radius ball is of radius 1 (or any other granularity) and the previous erosion step used is the preceding step. It should be appreciated that a ball of radius 1 has a diameter D of 3 voxels, since only (D−1)/2 voxels are eroded. In some cases, the use of such a small ball will cause artifacts, due to the discrete nature of the voxels. Preferably, different types of balls are used for alternating erosion steps. In a preferred embodiment of the invention three types of radius 1 balls are used: a complete 3×3×3 CUBE ball; a center voxel with six neighbors (CROSS ball); and a 3×3×3 cube with the corners CHOPPED off. The ball types are preferably alternated in the following order: (cross, full, chopped, cross, full, cross, chopped, cross, full, cross, cross, full, cross, cross, full, cross, cross) the series is continued as repetitions of {full, cross, cross}.

In a preferred embodiment of the invention, the distances between interior voxels and the boundaries are calculated using wave propagation from the cavity boundaries. Preferably, a graph is built using the voxels and a breadth first search is performed on the graph. Preferably, a ball of radius one is used to determine neighbors of a vortex. Alternatively or additionally, the distances can be calculated using Dijkstra's method. Preferably, approximate real distances are calculated, rather than by adding up unit values of distances between voxel centers. Preferably, the distance data is represented using a floating point representation.

In accordance with a preferred embodiment of the invention, the tissue is segmented into cavity interior voxels through which the path must pass and cavity boundary voxels, through which the path may not pass. Alternatively, a segmented data set is provided. In a preferred embodiment of the invention, the boundary and interior segments are identified based on a CT number and/or connectivity, as is well known in the art. Segmentation using thresholding is described, for example, in "Handbook of Pattern Recognition and Image Processing", edited by T. Y. Young and K. S. Fu, Academic Press, pp. 224–225, the disclosure of which is incorporated herein by reference. Alternatively, other methods such as are well known in the art, may be used to accomplish segmentation. In a preferred embodiment of the invention, especially preferred where data set 10 is segmented into a plurality of different tissue types, a user indicates to the system which tissues are interior and which are exterior. Alternatively, the user indicates tissue at the boundary of the cavity and marks it as exterior tissue voxels. It should be appreciated that the interior voxels need not be empty voxels. For example, a path can be planned which navigates a bone, with the fat and muscle tissue surrounding the bone being considered exterior tissues.

In a preferred embodiment of the invention, segmentation is performed manually, using tools such as thresholding and connectivity. Preferably, the tissue is eroded for the connectivity determination, to smooth over small errors.

In accordance with a preferred embodiment of the invention, a user enters various parameters which can be use to restrict the range of possibilities for the automatic path generation. In accordance with a preferred embodiment of the invention, at least some of the parameters are associated with rigid restrictions. Alternatively or additionally, at least some of the parameters are associated with flexible restrictions, which can be traded-off with at least some other parameters. This trade-off is preferably achieved by defining a composite path grading function including a relative weighting of different restrictions. Flexible restrictions are preferably defined using a graded penalty function. Rigid restrictions are preferably defined using a penalty function which achieves infinite penalty when the restriction is violated. Preferably, the penalty function has a zero penalty if the restriction is not violated. Alternatively, the penalty function is graded also for the non-violating situations, so that it may be considered to be a flexible restriction in those situations. In a preferred embodiment of the invention, the penalty for a voxel is determined by adding up a plurality of penalties, each cause by violation and/or partial violation of a restriction.

In accordance with a preferred embodiment of the invention, the system stores a plurality of sets of restrictions/input parameters, which a user can choose between and/or modify. Preferably, at least some of these sets are designed to provide optimal paths for certain tasks. In one preferred embodiment of the invention, a set is defined which causes the generation of a path which meets the restrictions posed by using a physical endoscope. Thus, it is easier to simulate what an actual endoscope will view. Preferably, when simulating an endoscope, the path is restricted to a maximum bend which is dependent on the particular endoscope and the width of the passage against whose walls the endoscope is pressed. Preferably, the viewing characteristics of such an endoscope are also simulated by the viewport and/or during the image generation. Preferably, these viewing characteristics include the lens type of the endoscope.

In preferred embodiments of the invention, at least some of the following parameters may be entered by a user:

(a) granularity, preferably including parameters for determining local granularity;

(b) allowed distance of path from the wall;

(c) penalty function, preferably entered as parameters to one of a set of predefined parametric penalty functions and/or distance functions or as a look-up table;

(d) desired amount and/or type of smoothing, preferably including limitations on smoothing responsive to the morphology of the passage, for example, passage width;

(e) viewing parameters, preferably including, maximum desired twist and other types of motion of viewport, field of view, distortion of field of view, shape and aspect ratio of field of view, preferably organized as sets corresponding to optical properties of various invasive tools;

(f) parameters for simulation of mechanical properties of invasive tools, preferably including a path dependent penalty function; and (g) rendering and display parameters, such as, colors, false color scheme, shading, illumination and path thereof, reflections and relative transparency of tissues.

In accordance with a preferred embodiment of the invention, a user may supply parameters which define and/or determine what is meant by the quality of the generated view. Such parameters may be determined, inter alia, by perceptual considerations, task-specific considerations and/or comfort of viewing considerations. It should be appreciated that the quality of view will generally be affected also by the above listed parameters. In a preferred embodiment of the invention, these parameters include at least one of:

(a) a maximum allowed speed;

(b) maximum allowed twist rate of the viewport;

(c) maximum allowed change in various viewing parameters; and (d) portions of the data set which the user want to view at such suitable parameters, possible the entire inner surface of the cavity.

In a preferred embodiment of the invention, the path and angular orientation of the viewport origin and/or of the viewport are automatically generated so that the portions which are desired to be viewed are within comfortable viewing conditions.

In a preferred embodiment of the invention, the generated path is smoothed, to reduce jerkiness in the view. Preferably, at least some of the above desired viewing quality parameters are met as a result of this smoothing. Preferably, after the smoothing, the path is analyzed to determine if it passes too close to boundary voxels and/or violates other restrictions. Preferably, the path is not smoothed at portions of the path which are very close to cavity boundaries and/or in narrow passages. Alternatively or additionally, different types of smoothing are applied responsive to the path characteristics and/or cavity morphology and/or passage width.

In accordance with a preferred embodiment of the invention, the smoothing is a linear combination between a point and its neighbors. Preferably one neighbor on each side is used, and the relative weighting is {0.3, 0.4, 0.3}. In accordance with a preferred embodiment of the invention, the entire path is smoothed a number of times, preferably seven times. Preferably, portions of the path which are closer than a predetermined distance to the boundary are not smoothed. Alternatively or additionally, the number of times a point is smoothed and/or the weights used and/or the type of smoothing is dependent on the distance from the boundary. Preferably, smoothing is not performed at the goal points. Alternatively, smoothing is performed at least at the starting and ending points.

In a preferred embodiment of the invention, at least one of the viewing parameters is also smoothed, so that changes in its values are smoother. In one preferred embodiment of the invention, a desired angular resolution is required for the viewing of various portions of data set 10. Preferably, when such an angular field of view requires a change in the field of view, these changes in field of view are smoothed.

In a preferred embodiment of the invention, the view aiming point is chosen to be a point along the path, forward of the view origin point. The location of the view aiming point is preferably determined responsive to the local bending at the view origin point and/or to the distance to the boundary, i.e. the distance between the two points is inversely dependent on the local bend and proportional to the distance to the boundary. As a result, in tight portions of the path, the view aiming point is relatively closer to the view origin point and so a smoother viewing angle is obtained. Alternatively or additionally, the view aiming point location may be dependent on the path and/or boundary characteristics at the projected view aiming point and/or a portion of the future path.

In most, if not all, medical images, the existence of noise is a very important consideration. Usually, acquiring images with a lower noise level increases the exposure of a patient to ionizing and/or otherwise dangerous radiation. In addition, many medical images have various types of artifacts. One problem caused by noise is that the boundary of the cavity may have holes in it, where a noise value has replaced or mutated the original, exterior voxel value. In a preferred embodiment of the invention, such holes are ignored, since in order for the path to pass through such a hole, it must pass very close to boundary voxels, which is extremely "undesirable", as a function of the distance function.

One problematic situation is when two cavities pass close together, such as is typical of the bowel. The addition of noise and/or partial volume artifacts may cause the boundary between the two cavities to disappear at certain locations. However, in accordance with a preferred embodiment of the invention, small missing portions of the boundaries are ignored since in order to pass through them, a penalty cost must be paid. Cavity enlargements and/or distortions caused by partial volume effects are generally not an issue in some preferred embodiments of the invention, since the path does not usually pass near the boundaries in these embodiments and/or is not affected by small variations in the boundary texture.

Another problem possibly caused by noise, is the creation of exterior tissue voxels in the middle of the cavity space. In a preferred embodiment of the invention, small groups of exterior tissue voxels, which are spaced from other exterior tissue voxels, are ignored during various steps of the path planning, such as during distance calculation and/or by allowing the path to pass through the voxels. The number, extent and separation of these voxels is preferably a parameter of the algorithm. Additionally or alternatively, preferably depending on the grouping of the suspected noise voxels, these voxels are removed during segmentation.

In accordance with a preferred embodiment of the invention, not all the voxels in the cavity are considered during the path determination. Rather, only a subset of the voxels are considered. Preferably, this subset is generated by creating a skeleton of the cavity.

Figure 5A:
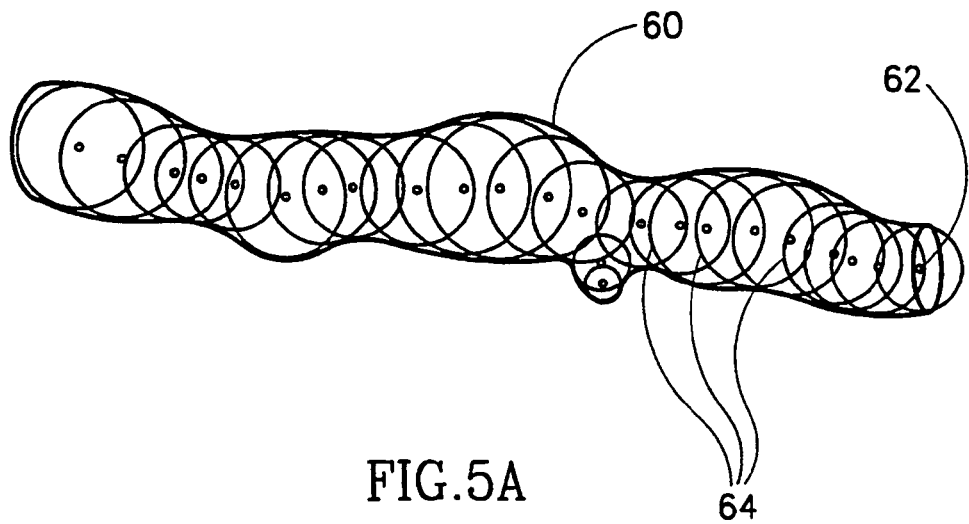
FIG. 5A is a schematic illustration of a skeletonized cavity, in accordance with a preferred embodiment of the invention.

FIG. 5A is a schematic illustration of a skeletonized cavity 60, in accordance with a preferred embodiment of the invention. Skeletonization is described for example in "An introduction to Morphological Image Processing" by E. R. Dougherty, SPIE Press, 1992, pp. 42–48, the disclosure of which is incorporated herein by reference. The skeleton of a body is defined as a set of points which are the centers of maximal balls which are bound by the body and which are not included in any other such bound ball (overlap is allowed). Such a skeleton generally retains the morphological features of the body. In FIG. 5A, a two-dimensional skeletonization including only a small subset 64 of the maximal balls, is shown. A skeleton 62 is a set of points which generally follows the contours of the body. In some preferred embodiments of the invention, only voxels which overlap the skeleton or within a certain radius from the skeleton are considered for the path. This radius may, in some preferred embodiments of the invention, be dependent on local morphology of the cavity. Once the path is determined, it will usually need to be interpolated and/or resampled to provide view origin points, which may, in some embodiments of the invention, lay between skeleton voxels. Alternatively or additionally, the determined path is smoothed, so that it may include voxels other than from the skeleton.

In accordance with a preferred embodiment of the invention, a graph is generated from voxels of the skeleton. In a preferred embodiment of the invention, the arcs of the graph are generated by defining neighbors for each voxel of the skeleton. Preferably all the voxels of the skeleton which are within a predetermined distance of a particular voxel, are connected to the voxel. Alternatively or additionally, the distance is determined responsive to the number of nearby voxels. Alternatively or additionally, the distance is determined responsive to the morphology of the cavity.

In a preferred embodiment of the invention, portions of the graph are constructed only when actually needed, using lazy evaluation techniques.

Figure 5B:
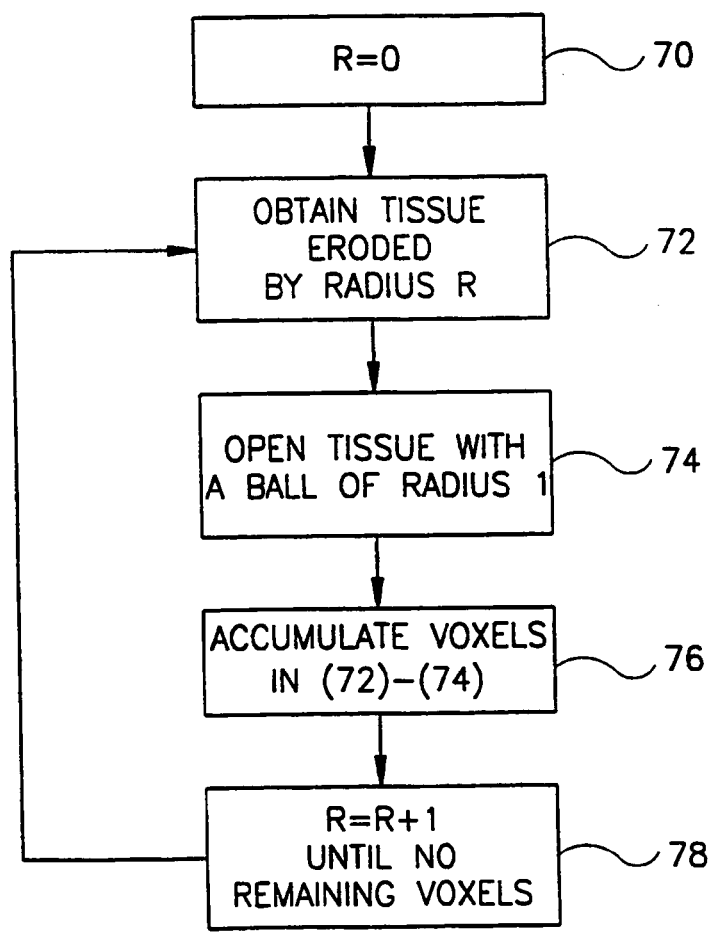
FIG. 5B is a flowchart of a method of skeletonization, in accordance with a preferred embodiment of the invention.

FIG. 5B is a flowchart of a method of skeletonizing, in accordance with a preferred embodiment of the invention. This method is based on maximal balls with a radius r being equivalent to opening with a ball of radius 1, a data set which was previously eroded with a ball of radius r. Opening is a composite process comprising eroding and then dilating (adding a layer). Thus, in accordance with a preferred embodiment of the invention, a skeleton is generated at the same time as the distance function, utilizing the partially eroded data set as an input. In the figure, the starting skeletonization radius is set (70) to zero. As with erosion, values other than zero may be selected and they affect the precision of the skeleton and/or may smooth the cavity morphology and/or reduce the effects of noise. Tissue eroded by a ball of radius r (72) is opened with a ball of radius 1 (74). Voxels which are removed by the opening operation, correspond to centers of maximal balls of radius r and are preferably accumulated and added to the skeleton (76). It should be noted that opening comprises eroding and then dilating. The above described process of erosion also generates a data set which includes the effect of eroding with a ball of radius 1, the result of an erosion with a ball of radius r.

In some preferred embodiments of the invention, the data set is represented using polygons, which described surfaces of the boundary, alternatively to or in addition to using voxels. Preferably, the inside of the cavity is determined using a 3D paint function and/or may be known from the segmentation and/or may be determined when the polygon data is generated from the image data. Preferably, this determination is made for points on a grid. Distance calculation may be performed using the same grid. For each point on the grid, which is interior to the cavity, the distance to the nearest polygon is determined. Preferably, and especially where the polygons have a bounded size, locality functions are used to limited the number of polygons which are tested. In a preferred embodiment of the invention, a penalty function may be defined in which any distance to the boundary above a certain distance has the same penalty value. Thus, if there are no polygons within that distance, there is no need to look further and calculate the distance. Thereafter, the path finding method may be applied to the grid points using the determined distance function. Preferably, the calculated distance is used to determine a skeleton of the grid.

In a preferred embodiment of the invention, the viewport is directed to a view aiming point along the path. Alternatively or additionally, the view aiming point moves along a different trajectory. In a preferred embodiment of the invention, the view aiming point spirals around path 16, so that the viewing direction is substantially perpendicular to the path. This type of path is useful for a careful survey of the inside of a cavity, for example, for colonscopy. Alternatively to a substantial perpendicular angle, any other angle may be used, especially to assure an overlap between consecutive images and/or portions of the spiral. Preferably, the viewport is also slightly twisted so that the axes of all the individually generated frames may be made as parallel as possible.

In accordance with a preferred embodiment of the invention, portions of data set 10, which are not displayed or are not displayed within desired parameters, are indicated to the user. In one preferred embodiment of the invention, they are indicated separately from the endoscope-eye view, preferably on a plan-view or on a three-dimensional perspective view. Alternatively or additionally, these indications are overlaid as symbols on the real-time virtual endoscope view.

In accordance with a preferred embodiment of the invention the view is rendered using a raycasting method, for example as described in U.S. provisional application Ser. No. 60/075,519 titled "Raycasting System and Method", filed on Feb. 23, 1998, by applicants S. Akerman and G. Miller, the disclosure of which is incorporated herein by reference. Preferably, the distance from the boundary which is determined for each point along the path, is used as a lower limit for the ray casting algorithm, since there can be no exterior voxels closer than the determined distance.

Although the above methods are generally described as including the planning of all the aspects of the path in a preferred embodiment of the invention, the above described methods are used for only some of the aspects. Alternatively or additionally, the order of steps may be changed and/or steps split into sub-steps and/or combined. In a preferred embodiment of the invention, lazy evaluation techniques are utilized, to delay heavy computations and/or reduce memory requirements as much as possible. Such computations include, evaluating a penalty function and/or constructing a graph.

In a preferred embodiment of the invention, a user performs real-time control of various viewing parameters while viewing a path generated in accordance with a preferred embodiment of the invention. Such parameters may include illumination parameters, such as position, movement and decay as a function of distance, speed, direction of gaze, angle of gaze, field of view size and aspect ratio.

In accordance with some preferred embodiments of the invention, some of the methods described herein are applied in an iterative manner. In one preferred embodiment of the invention, a user enters limitations, the system generates a path which attempts to meet these limitations and then the user possibly changes these limitation, based on the quality of the generated path and/or the generated view. Preferably, at least some of the computations, such as distance computations, are performed only once and not repeated each iteration. Additionally, preferably not all the limitations need to be entered each iteration. One example of user entered limitations is a set of points through which it is desired that the path pass.

Additionally or alternatively, the above described methods may be applied as a post processing step to a path generated by other means and/or entered by a user, especially for smoothing such a path and/or for calculation of viewing parameters. In one preferred embodiment of the invention, only optimal viewing angles and velocities are determined for a fixed path. In a preferred embodiment of the invention, the methods are used to select a path from a (preferably small) set of paths. Additionally or alternatively, the above described methods may be applied to evaluate an existing path, especially after a user modified it or if it was smoothed, to determine if any user selected restrictions are violated and/or to assign a grade of viewing quality to the path. Preferably, the methods are used to grade possible paths to aid a user in selecting one of these paths.

In accordance with a preferred embodiment of the invention, an existing path may be optimized by generating a graph which includes only voxels included in and within a certain distance from the path and applying the path finding methods on that graph. Preferably, the width of the graph is dependent on the local and/or typical width of the cavity.

It should be appreciated that the methods described herein may also be used to add a goal point in the middle of an existing path and/or to connect two paths smoothly. In some cases, only the smoothing portions of the algorithm may be applied. Alternatively, a graph may be generated which includes a region surrounding the point to be added to the graph and/or at which the graph are connected and a path optimizing method may be applied to that (local) graph.

In accordance with a preferred embodiment of the invention, goal points entered by a user are moved slightly so that sharp bends in the path are reduced. Alternatively or additionally, goal points are moved so that they are at more desirable location. Such motion is preferably limited to a small distance and/or a small number of dimensions. Preferably, these points are moved perpendicular to the path and/or the tissue boundary, depending on what stage of processing these points are moved.

In accordance with a preferred embodiment of the invention, more than one tissue may be included in the interior voxels and/or the exterior voxels. Additionally or alternatively, at least one tissue-type may be defined to be semi-transparent. Additionally or alternatively the type of tissue at a voxel may affect the penalty of passing through that voxel. Alternatively or additionally, it is desirable that the path passes through a minimum number of tissue boundaries. This is preferably achieved by assigning passing between tissue type a high penalty (but preferably not an infinite penalty). Preferably, the penalty is a function of the distance from the boundary between the tissues.

In a preferred embodiment of the invention, tissue types are stored by using a bit-volume for each tissue type with a value of "1" for all the voxels which are of the tissue type. Alternatively, each voxel may be assigned a value which indicates a tissue type. As can be appreciated, a single voxel may, in some cases, be assigned more than one tissue type.

In a preferred embodiment of the invention, the penalty function depends on the distance from different tissue types. For example, it may be less desirable to be within 5 voxels of tissue type A than within 5 voxels of tissue type B. Preferably, a different distance is calculated for each tissue type. Alternatively only the distance to the closest tissue is calculated.

In a preferred embodiment of the invention, a given tissue may be less desirable for travel, but travel therethrough may be allowed. Preferably, the penalty function is not infinite for that tissue, as it preferably is for exterior voxels. It should be appreciated that an exterior type tissue may also be transparent and/or semi-transparent.

In a preferred embodiment of the invention, different tissue types are indicated using transparent hued voxels and/or using volume textures.

In a preferred embodiment of the invention, two or more data sets are registered and displayed together. Two such data sets may be acquired at different times, using different modalities and/or may be of the same tissue but at different phase of cyclic motion thereof. Preferably, the path is constrained to pass within a cavity which is defined by the intersection of all the cavities.

It should be appreciated that in some preferred embodiments of the invention, a trajectory may not be continuous. For example, a trajectory of the view origin may consist of segments. In another example, the view aiming point may have a very fragmented trajectory. However, since the generated view is often viewed in a serial manner, the word trajectory is used to described the progression of the view origin and/or the aiming point from the first frame of the view to the last frame. In addition, it should be noted that even a continues trajectory comprises a finite number of discrete points at which a view is generated.

It should be appreciated that the above described methods of automatic path determination, as described hereinabove contain many features, not all of which need be practiced in all embodiments of the invention. Rather, various embodiments of the invention will utilize only some of the above described techniques, features or methods and or combinations thereof. In addition, although the above description is focused on methods, apparatus for performing these methods is also considered to be within the scope of the invention. Additionally or alternatively, other methods of path finding may be used. In accordance with a preferred embodiment of the invention, methods known for penalty optimization are applied to determine an optimal path between the goal points in view of penalties assigned as described hereinabove.

It will be appreciated by a person skilled in the art that the present invention is not limited by what has thus far been described. Rather, the present invention is limited only by the claims which follow.

The invention claimed is:

1. A method of path planning, comprising:
providing a medical imaging dataset representing a cavity and a boundary;
providing a plurality of points in said dataset, including at least a starting point and an ending point;
automatically determining a path between the starting point and the ending point, responsive to a penalty function defined by penalty values associated with passing through various points in the cavity; and
selecting a data granularity level for said path determination.

2. A method according to claim 1, wherein automatically determining a path comprises evaluating a penalty function for the points.

3. A method according to claim 2, wherein said penalty function is dependent on the distance of the point from a boundary of the cavity.

4. A method according to claim 3, wherein said penalty function is lower for points which are further from the boundary.

5. A method according to claim 1, wherein said granularity is determined responsive to a morphology of said cavity.

6. A method according to claim 5, wherein a local granularity is determined and wherein said morphology comprises a local morphology.

7. A method according to claim 6, wherein said local morphology comprises a local width.

8. A method according to claim 1, wherein a local granularity is determined and wherein said granularity is determined responsive to a distance of a locality from a cavity boundary.

9. A method according to claim 1, wherein a first granularity is determined for a first path planning and comprising repeating said path planning using a second granularity and using said first path as a starting point for said repeated path planning.

10. A method of path planning, comprising:
providing a medical imaging dataset representing a cavity and a boundary;
providing a plurality of points in said dataset, including at least a starting point and an ending point; and
automatically determining a path between the starting point and the ending point, responsive to a penalty function defined by penalty values associated with passing through various points in the cavity, wherein said determining a path comprises determining a relatively short path.

11. A method according to claim 10, wherein said penalty function is responsive to a morphology of the cavity.

12. A method according to claim 11, wherein said morphology comprises a width.

13. A method according to claim 11, wherein said morphology is a local morphology.

14. A method according to claim 10, wherein said penalty function is responsive to the path.

15. A method according to claim 14, wherein said penalty function is responsive to an amount of local bending of the path.

16. A method according to claim 10, wherein automatically determining a path comprises automatically determining a trajectory of an origin of a viewport.

17. A method according to claim 10, wherein providing a plurality of points comprises providing a trajectory.

18. A method according to claim 10, wherein automatically determining a path comprises automatically determining a trajectory of an aiming point.

19. A method according to claim 10, wherein a relatively short path comprises a shortest path which takes into consideration the penalty value associated with the various locations.

20. A method according to claim 10, wherein automatically determining a path comprises generating a graph representing at least a portion of the cavity.

21. A method according to claim 20, wherein said path is determined by applying a path finding method to the graph and wherein said portions of said graph are generated only when needed by said method.

22. A method according to claim 20, wherein automatically determining a path comprises determining a path using Dijkstra's shortest path finding method on said graph.

23. A method according to claim 20, wherein said graph includes only a subset of voxels in said cavity.

24. A method according to claim 23, wherein said graph comprises substantially only a skeleton of said cavity.

25. A method according to claim 24, wherein said skeleton is found utilizing data from erosion of the cavity, which erosion is utilized to determine a distance of interior points from said boundary.

26. A method according to claim 10, wherein said dataset is represented by voxels.

27. A method according to claim 10, wherein said boundary is represented by polygons.

28. A method according to claim 10, wherein said dataset comprises a CT dataset.

29. A method according to claim 10, wherein said dataset comprises an MRI dataset.

30. A method according to claim 10, wherein said dataset comprises a NM dataset.

31. A method of path planning, comprising:
providing a medical imaging dataset representing a cavity and a boundary;
providing a plurality of points in said dataset, including at least a starting point and an ending point; and
automatically determining a path between the starting point and the ending point, responsive to a penalty function defined by penalty values associated with passing through various points in the cavity, wherein automatically determining a path comprises evaluating a penalty function for the points, said penalty function being dependent on the distance of the point from a boundary of the cavity, and said penalty function being lower for points which are further from the boundary, wherein said penalty function has a substantial rate of increase when approaching said boundary.

32. A method of path planning, comprising:
providing a medical imaging dataset representing a cavity and a boundary;
providing a plurality of points in said dataset, including at least a starting point and an ending point; and
automatically determining a path between the starting point and the ending point, responsive to a penalty function defined by penalty values associated with passing through various points in the cavity, wherein automatically determining a path comprises evaluating a penalty function for the points, said penalty function being dependent on the distance of the point from a boundary of the cavity, and said penalty function being lower for points which are further from the boundary, wherein said penalty function has a low rate of change away from said boundary.

33. A method of path planning, comprising:
providing a medical imaging dataset representing a cavity and a boundary;
providing a plurality of points in said dataset, including at least a starting point and an ending point;
automatically determining a path between the starting point and the ending point, responsive to a penalty function defined by penalty values associated with passing through various points in the cavity, wherein automatically determining a path comprises evaluating a penalty function for the points, said penalty function being dependent on the distance of the point from a boundary of the cavity; and
determining said distance by erosion of the dataset.

34. A method of path planning, comprising:
providing a medical imaging dataset representing a cavity and a boundary;
providing a plurality of points in said dataset, including at least a starting point and an ending point;
automatically determining a path between the starting point and the ending point, responsive to a penalty function defined by penalty values associated with passing through various points in the cavity, wherein automatically determining a path comprises evaluating a penalty function for the points, said penalty function being dependent on the distance of the point from a boundary of the cavity; and
determining said distance by wave propagation from the boundaries of said cavity.

35. A method of path planning, comprising:
providing a medical imaging dataset representing a cavity and a boundary;
providing a plurality of points in said dataset, including at least a starting point and an ending point; and
automatically determining a path between the starting point and the ending point, responsive to a penalty function defined by penalty values associated with passing through various points in the cavity, wherein said boundary has small holes therein and wherein said path does not pass through holes narrower than a predetermined width.

36. A method according to claim 35, wherein said predetermined width is dependent on a morphology of the cavity.

37. A method of path planning, comprising the steps of:
providing a medical dataset representing a cavity having a plurality of bends and a boundary;
providing a plurality of points in said dataset, including at least a starting point and an ending point; and
automatically determining a path between the starting point and the ending point, wherein said path does not remain substantially in a medical axis of the cavity and does not approach closer than a predetermined distance to said boundary, in at least two of said bends;
wherein said dataset is represented using voxels and wherein said path does not approach closer than three voxels to said boundary.

38. A method of path planning, comprising the steps of:
providing a medical dataset representing a cavity having a plurality of bends and a boundary;
providing a plurality of points in said dataset, including at least a starting point and an ending point; and
automatically determining a path between the starting point and the ending point, wherein said path does not remain substantially in a medical axis of the cavity and does not approach closer than a predetermined distance to said boundary, in at least two of said bends;
wherein said dataset is represented using voxels and wherein said path does not approach closer than one tenth the local width of said cavity, to said boundary.

39. A method of path planning, comprising the steps of:
providing a medical dataset representing a cavity having a plurality of bends and a boundary;
providing a plurality of points in said dataset, including at least a starting point and an ending point; and
automatically determining a path between the starting point and the ending point, wherein said path does not remain substantially in a medical axis of the cavity and does not approach closer than a predetermined distance to said boundary, in at least two of said bends;
wherein said dataset is represented using voxels and wherein said path does pass through holes in said boundary which are narrower than a predetermined width.

40. A method of simultaneously distance determining and skeletonizing a dataset including a cavity and a boundary thereof, comprising:
eroding said cavity, using a series balls of increasing radius $R_i$;
determining a distance of points interior to the cavity, from the boundary, utilizing said erosion;
opening said eroded cavity, for each radius $R_i$, using a ball of radius 1; and
accumulating the points which are removed from said eroded cavity by said opening, to form a skeleton.

41. A method according to claim 40, wherein erosion by a ball R comprises eroding the result of eroding with a ball of radius R−1, with a ball of radius 1.

42. A method of path planning, comprising the steps of:
providing a dataset representing a cavity and a boundary;
providing a plurality of points in said dataset, including at least a starting point and an ending point; and
automatically determining a path between the starting point and the ending point, responsive to a penalty function defined by penalty values associated with passing through various points in the cavity, wherein automatically determining a path comprises evaluating a penalty function for the points, wherein said penalty function is dependent on the distance of the point from a boundary of the cavity, and wherein said penalty function is lower for points which are further from the boundary.

43. A method of path planning, comprising the steps of:
providing a dataset representing a cavity and a boundary;
providing a plurality of points in said dataset, including at least a starting point and an ending point; and
automatically determining a path between the starting point and the ending point, responsive to a penalty function defined by penalty values associated with passing through various points in the cavity, wherein said determining a path comprises determining a relatively short path.

44. A method according to claim 43, wherein a relatively short path comprises a shortest path which takes into consideration the penalty value associated with the various points.

45. A method according to claim 43, wherein automatically determining a path comprises generating a graph representing at least a portion of the cavity and wherein said path is determined by applying a path finding method to the graph and wherein said portions of said graph are generated only when needed by said method.

46. A method of path planning, comprising the steps of:
providing a medical imaging dataset representing a cavity and a boundary;
providing a plurality of points in said dataset, including at least a starting point and an ending point; and
automatically determining a path between the starting point and the ending point, responsive to a penalty function defined by penalty values associated with passing through various points in the cavity, wherein said penalty function is responsive to an Euclidean distance of said various points from said boundary.

47. A method of path planning, comprising the steps of:
providing a medical imaging dataset representing a cavity and a boundary;
providing a plurality of points in said dataset, including at least a starting point and an ending point; and
automatically determining a path between the starting point and the ending point, responsive to a penalty function defined by penalty values associated with passing through various points in the cavity, wherein said path planning allows a path to pass through two diagonally-adjacent voxels.

* * * * *